(12) United States Patent
Misu (10) Patent No.: US 8,092,079 B2
(45) Date of Patent: Jan. 10, 2012

(54) METHOD FOR DETERMINING WHETHER A LIQUID IS PROPERLY STIRRED

(75) Inventor: Takahiro Misu, Tokyo (JP)

(73) Assignee: Beckman Coulter, Inc., Brea, CA (US)

( * ) Notice: Subject to any disclaimer, the term of this patent is extended or adjusted under 35 U.S.C. 154(b) by 95 days.

(21) Appl. No.: 12/262,616

(22) Filed: Oct. 31, 2008

(65) Prior Publication Data

US 2009/0113998 A1    May 7, 2009

(30) Foreign Application Priority Data

Nov. 2, 2007 (JP) .................................. 2007-286012

(51) Int. Cl.
    G01N 25/00    (2006.01)
(52) U.S. Cl. .......... 374/45; 374/101; 374/102; 374/107; 374/141; 374/142; 73/1.02; 73/53.01; 73/584; 366/118
(58) Field of Classification Search .................. None
    See application file for complete search history.

(56) References Cited

U.S. PATENT DOCUMENTS 5,033,321 A * 7/1991 Gerson ........................... 73/866
6,875,401 B1 * 4/2005 Suzuki et al. .................. 422/63
2005/0150830 A1 * 7/2005 Laugharn et al. ............. 210/634
2010/0135352 A1 * 6/2010 Tsuda .............................. 374/45

FOREIGN PATENT DOCUMENTS

JP    2006-119125    5/2006

OTHER PUBLICATIONS

Chen, J. et al. "Study of anisotropic etching of (1 0 0) Si with ultrasonic agitation," Sensors and actuators A 2002, 96, 152-156.*

* cited by examiner

*Primary Examiner* — Yelena G Gakh
*Assistant Examiner* — Michelle Adams
(74) *Attorney, Agent, or Firm* — Kilpatrick Townsend & Stockton LLP (57) ABSTRACT

A stirring determination method uses an analyzer in which a liquid contained in a vessel is stirred by an acoustic wave generated by an acoustic wave generating unit attached to the vessel, optical characteristics of a reaction solution obtained by stirring the liquid are measured, and the reaction solution is analyzed based on the optical characteristics of the reaction solution. The method includes measuring a temperature of the liquid in a position where the temperature of the liquid is different before and after the liquid is stirred; and determining whether the liquid is properly stirred based on a rate of increase in the measured temperature of the liquid.

6 Claims, 13 Drawing Sheets

METHOD FOR DETERMINING WHETHER A LIQUID IS PROPERLY STIRRED

CROSS-REFERENCE TO RELATED APPLICATIONS

This application is based upon and claims the benefit of priority from Japanese Patent Application No. 2007-286012, filed Nov. 2, 2007, the entire contents of which are incorporated herein by reference.

BACKGROUND OF THE INVENTION

1. Field of the Invention

The present invention relates to a stirring determination method and an analyzer.

2. Description of the Related Art

Known analyzers are configured to contactlessly stir liquid stored in a reaction vessel with acoustic waves generated by an acoustic wave generating device in order to prevent "carry-over" (for example, see Japanese Patent Application Laid-open No. 2006-119125). Such an analyzer stirs a specimen and a reagent, which are dispensed to a reaction vessel, with acoustic waves generated by a driven acoustic wave generating device to react the specimen and the reagent.

SUMMARY OF THE INVENTION

A stirring determination method according to an aspect of the present invention uses an analyzer in which a liquid contained in a vessel is stirred by an acoustic wave generated by an acoustic wave generating unit attached to the vessel, optical characteristics of a reaction solution obtained by stirring the liquid are measured, and the reaction solution is analyzed based on the optical characteristics of the reaction solution. The method includes measuring a temperature of the liquid in a position where the temperature of the liquid is different before and after the liquid is stirred; and determining whether the liquid is properly stirred based on a rate of increase in the measured temperature of the liquid.

An analyzer according to another aspect of the present invention includes an acoustic wave generating unit that generates an acoustic wave used to stir a liquid contained in a vessel to which the acoustic wave generating unit is attached; a temperature measuring unit that measures a temperature of the liquid in a position where the temperature of the liquid is different before and after the liquid is stirred; and a determining unit that determines whether the liquid is properly stirred based on a rate of increase in the measured temperature of the liquid. Optical characteristics of a reaction solution obtained by stirring the liquid is measured, and the liquid is analyzed based on the optical characteristics of the reaction solution.

The above and other objects, features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Exemplary embodiments of the present invention are explained in detail below with reference to the accompanying drawings.

Figure 1:
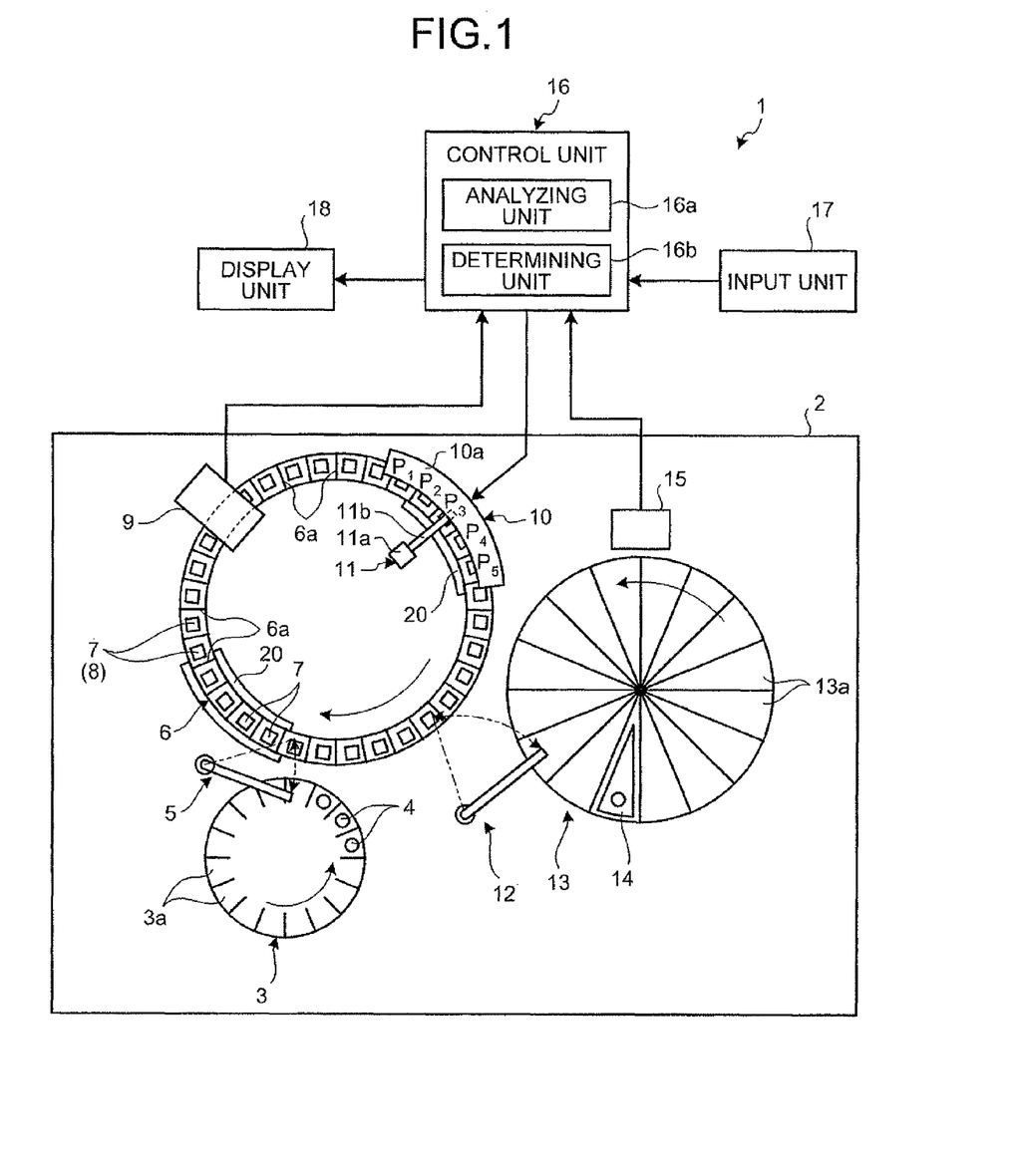
FIG. 1 is a schematic diagram of an automatic analyzer according to a first embodiment of the present invention.
Figure 2:
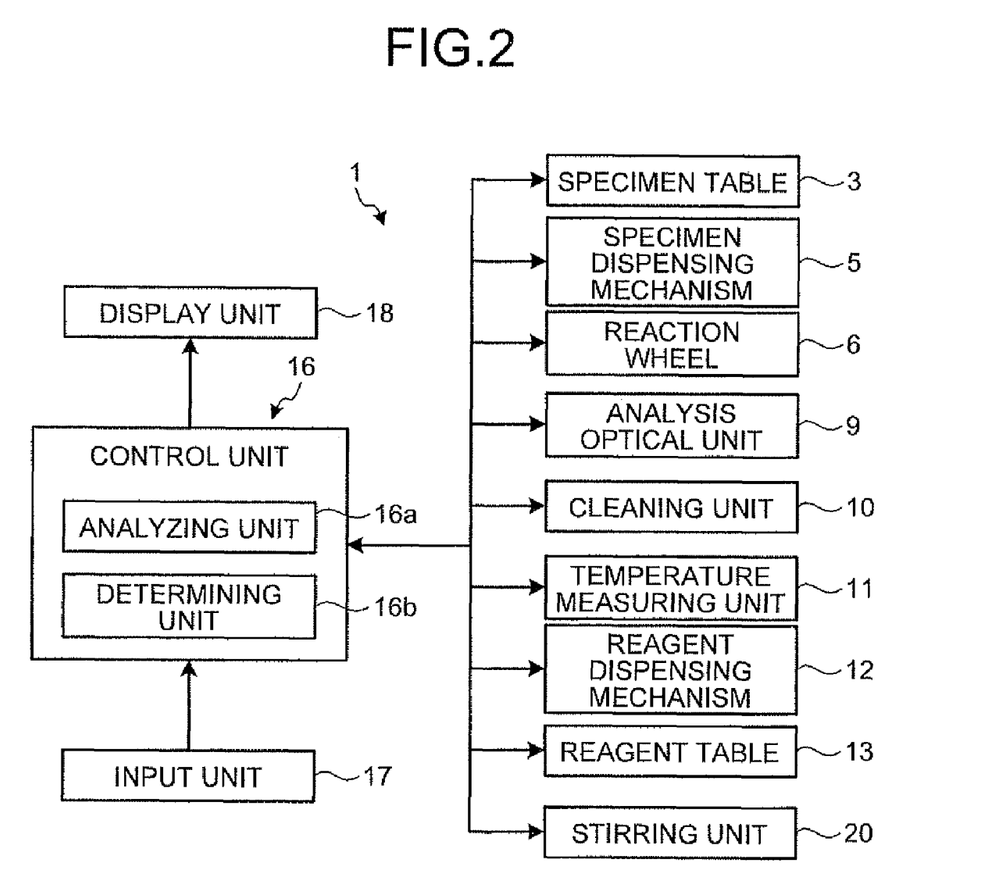
FIG. 2 is a block diagram of a configuration of the automatic analyzer.
Figure 3:
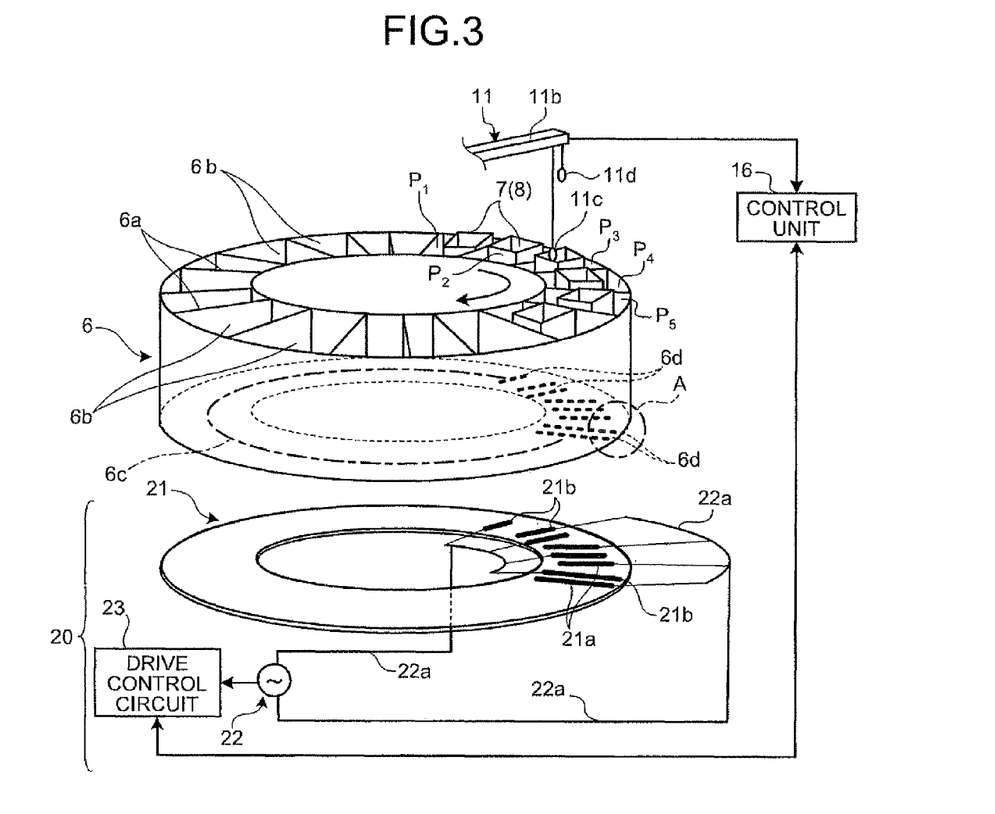
FIG. 3 is a schematic diagram of a stirring unit and shows a reaction wheel of the automatic analyzer of FIG. 1 as an enlarged view.

A stirring determination method and an automatic analyzer 1 according to a first embodiment of the present invention are explained below. FIG. 1 is a schematic diagram of the automatic analyzer 1. FIG. 2 is a block diagram of a configuration of the automatic analyzer 1. FIG. 3 is a schematic diagram of a stirring unit 20 and shows a reaction wheel 6 of the automatic analyzer 1 shown in FIG. 1.

As shown in FIGS. 1 to 3, the automatic analyzer 1 includes a specimen table 3, the reaction wheel 6, and a reagent table 13 in which they are arranged on a work table 2 and rotatable in their circumferential direction while being separated from each other, and also includes the stirring unit 20 containing a reaction vessel 7. The automatic analyzer 1 further includes a specimen dispensing mechanism 5 that is positioned between the specimen table 3 and the reaction wheel 6, and a reagent dispensing mechanism 12 that is positioned between the reaction wheel 6 and a reagent table 13.

As shown in FIG. 1, the specimen table 3 is rotated by a driving unit in the direction indicated by the arrow shown in FIG. 1. The specimen table 3 includes a plurality of storage rooms 3a that are arranged at equal intervals along the circumference of the specimen table 3. In each of the storage rooms 3a, a specimen vessel 4 containing a specimen is detachably stored.

The specimen dispensing mechanism 5 dispenses, to the reaction vessel 7, a smaller amount of specimen such as urine or blood than a reagent dispensed to the reaction vessel 7. Specifically, as shown in FIGS. 1 to 3, the specimen dispensing mechanism 5 sequentially dispenses the specimen from the specimen vessels 4 to the respective reaction vessels 7 housed in holders 6b of the reaction wheel 6.

Figure 4:
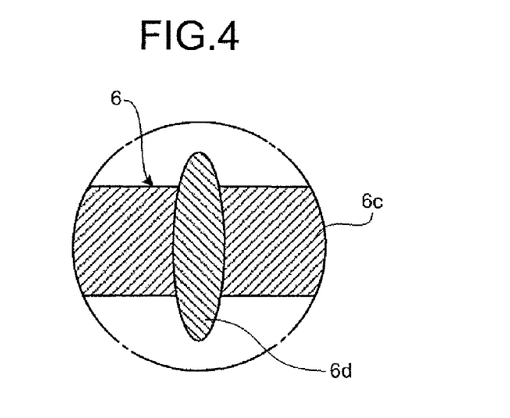
FIG. 4 is an enlarged cross sectional view of portion A shown in FIG. 3.

As shown in FIG. 1, the reaction wheel 6 is rotated by a driving unit different from that for driving the specimen table 3 in the direction indicated by the arrow shown in FIG. 1. The reaction wheel 6 includes a plurality of holders 6b sectioned by walls 6a at equal intervals in the circumferential direction of the reaction wheel 6. The reaction vessels 7 in each of which the specimen and the reagent react are detachably housed in the respective holders 6b. The holder 6b has openings on both sides of the holder 6b in the radial direction of the reaction wheel 6 through which light passes. As shown in FIGS. 3 and 4, a pair of positive and negative lead electrodes 6d that extend in the radial direction of the reaction wheel 6 and penetrate a bottom wall 6c of the reaction wheel 6. The reaction wheel 6 rotates clockwise one-fourth of "a revolution minus the angle occupied by one reaction vessel" for every cycler and rotates counterclockwise the angle corresponding to the reaction vessel 7 in four cycles. A terminal board 21 of the stirring unit 20 is arranged under the reaction wheel 6 (see FIG. 3), and the reaction wheel 6 is provided with an analysis optical unit 9 and a cleaning unit 10.

Figure 5:
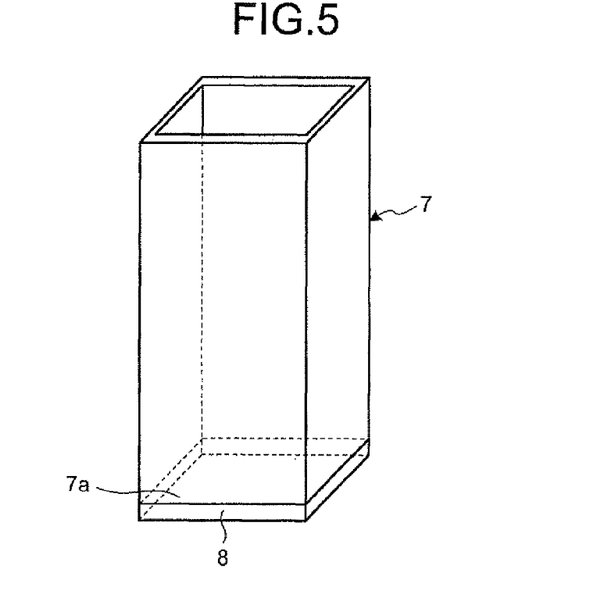
FIG. 5 is a perspective view of a reaction vessel to which a surface acoustic wave device used in the automatic analyzer is attached.
Figure 6:
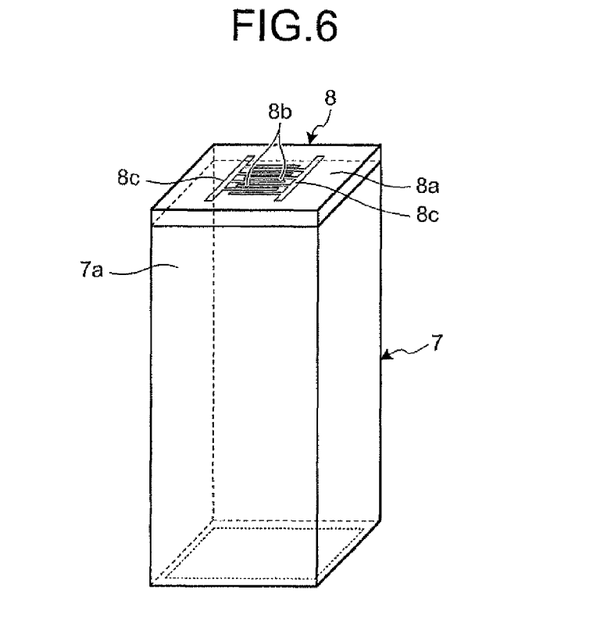
FIG. 6 is a perspective inverted view of the reaction vessel shown in FIG. 5.

As shown in FIGS. 5 and 6, the reaction vessel 7 is hexahedral and a surface acoustic wave device 8 is attached to the bottom surface of a bottom wall 7a of the reaction vessel 7. The reaction vessel 7 is made of, for example, a material that allows at least 80% of analysis light emitted from a light source to pass through, such as glass including heat-resistant glass or synthetic resin including cyclic olefins and polystyrene.

Figure 7:
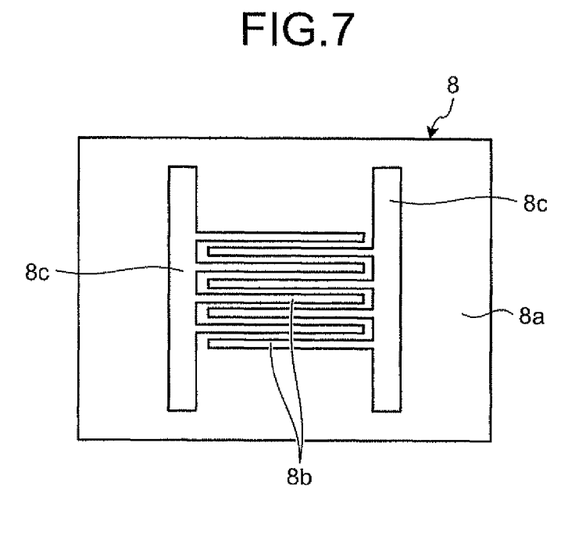
FIG. 7 is a plan view of the surface acoustic wave device attached to the reaction vessel.

As shown in FIGS. 6 and 7, the surface acoustic wave device 8 includes a piezoelectric substrate 8a made of a piezoelectric material such as lithium niobate ($LiNbO_3$), a transducer 8b formed of an interdigital transducer (IDT) and formed on the piezoelectric substrate 8a, and bus bars 8c formed on both sides of the transducer 8b. The surface acoustic wave device 8 is attached to the reaction vessel 7 such that the transducer 8b and the bus bar 8c are exposed to the outside. The surface of the surface acoustic wave device 8 that is attached to the reaction vessel 7 is flat. Each of the bus bars 8c is in contact with and thus is electrically connected to a corresponding one of a pair of lead electrodes 6d.

In the analysis optical unit 9, the light source emits analysis light for analyzing the reaction solution of the reagent and the specimen in the reaction vessel 7. The analysis light having passed through the reaction solution is received by a light receiving device that is opposed to the light source. The light receiving device outputs an optical signal corresponding to the amount of the received light to an analyzing unit 16a.

Figure 8:
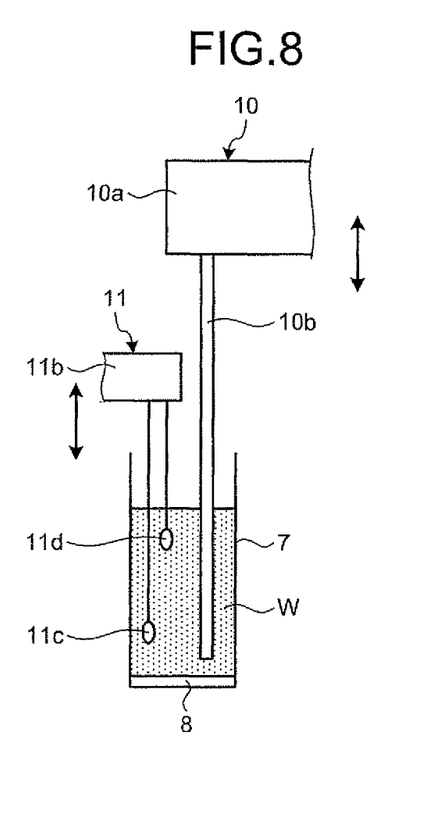
FIG. 8 is a schematic diagram of the reaction vessel into which a discharge nozzle of a cleaning unit and a temperature sensor of a temperature measuring unit are inserted.

As shown in FIG. 8, the cleaning unit 10 includes an elevating member 10a that moves up and down, a suction nozzle and a discharge nozzle 10b provided to the elevating member 10a. The suction nozzle sucks and removes the reaction solution from the reaction vessel 7, the discharge nozzle 10b discharges a cleaning solution such as a detergent and washing water W into the reaction vessel 7, and the suction nozzle sucks and removes the discharged washing water from the reaction vessel 7. This operation is repeated multiple times to clean the reaction vessel 7 after the analysis optical unit 9 measures the light. As shown in FIG. 1, the cleaning unit 10 sequentially cleans the five reaction vessels 7 located at positions P1 to P5, respectively, where P1 is the starting position of cleaning and P5 is the ending position of cleaning in the direction of rotation of the reaction wheel 6. After being cleaned, the reaction vessels 7 are used again for analyzing another specimen.

A temperature measuring unit 11 is opposed to the cleaning unit 10. The temperature measuring unit 11 measures the temperature of the washing water in the reaction vessel 7, which is discharged by the discharge nozzle 10b. The temperature measuring unit 11 is provided corresponding to the position P3 of the reaction vessel 7 in the direction of rotation of the reaction wheel 6. As shown in FIGS. 1, 3, and 8, the temperature measuring unit 11 includes a holding arm 11b attached to a support column 11a, and temperature sensors 11c and 11d hanging from the holding arm 11b. The holding arm 11b is rotatable on the support column 11a. The temperature sensors 11c and 11d are in different positions in the vertical direction, i.e., the temperature sensor 11c is closer to the bottom surface of the reaction vessel 7 and the temperature sensor 11d is closer to the surface of the washing water (hereinafter, "liquid surface").

As shown in FIG. 1, the reagent dispensing mechanism 12 sequentially dispenses the reagent from a predetermined one of reagent vessels 14 of the reagent table 13 to the reaction vessels 7 housed in the corresponding holder 6b of the reaction wheel 6.

As shown in FIG. 1, the reagent table 13 is rotated by a driving unit that is different from that for driving the specimen table 3 and the reaction wheel 6 in the direction indicted by the arrow. The reagent table 13 includes a plurality of fan-shaped storage rooms 13a formed along the circumference of the reagent table 13. The reagent vessels 14 can be detachably housed in the respective storage room 13a. The reagent vessel 14 are filled with respectively predetermined amounts of reagents corresponding to test items, and information recording medium showing information about the reagent, such as a barcode label, is attached to each of the reagent vessel 14.

Near the circumference of the reagent table 13, a reading device 15 is arranged. The reading device 15 reads the information about, for example, the type, lot, and expiry date of the reagent from the information recording medium attached to the reagent vessel 14, and outputs the information to the control unit 16.

As shown in FIG. 2, the control unit 16 is connected to units including the specimen dispensing mechanism 5, the analysis optical unit 9, the cleaning unit 10, the temperature measuring unit 11, the reagent dispensing mechanism 12, the reading device 15, an input unit 17, a display unit 18, and the stirring unit 20. The control unit 16 controls these units, is realized by, for example, a microcomputer. The control unit 16 includes the analyzing unit 16a and a determining unit 16b. When the control unit 16 determines that, for example, the lot or the expiry date of the reagent is out of the predetermined range based on the information read from the information recording medium, the control unit 16 controls the automatic analyzer 1 to restrict the analysis operation or gives a warning to an operator.

The analyzing unit 16a analyzes the reaction solution and obtains, for example, a component density of the specimen based on the absorbance of the reaction solution in the reaction vessel 7 obtained from the optical signal received from the light receiving device. The determining unit 16b determines whether liquid sample including the specimen and the reagent in the reaction vessel 7 is properly stirred based on the rate of increase in the temperature of the liquid sample (hereinafter, "temperature increasing rate") where the increase of the temperature is caused by the stirring unit 20 stirring the liquid sample.

The input unit 17 is for inputting the test item etc. to the control unit 16. For example, a keyboard and a mouse are used as the input unit 17. The display unit 18 displays, for example, the contents of analysis or a warning. For example, a display panel is used for the display unit 18.

The stirring unit 20 stirs a liquid contained in the reaction vessel 7 with acoustic waves. As shown in FIG. 3, the stirring unit 20 includes the terminal board 21, a signal generator 22, and a drive control circuit 23. The stirring unit 20 is positioned near the specimen dispensing mechanism 5 located outside of the reaction wheel 6, and the stirring unit 20 is provided to the cleaning unit 10. Hereinafter, only the stirring unit 20 provided to the cleaning unit 10 is explained, and explanation on the stirring unit 20 positioned near the specimen dispensing mechanism 5 is omitted because the corresponding units are labeled by the same reference numerals.

As shown in FIG. 3, the terminal board 21 is a ring-shaped insulating plate, and it is arranged under the reaction wheel 6. The terminal board 21 is not rotatable. The terminal board 21 includes contact electrodes 21a and 21b that are in contact with the lead electrodes 6d in a stirring area corresponding to the positions P2 to P5 of the reaction vessels 7 subsequent to the position P1 of the reaction vessel 7 from which cleaning is started, so that power is supplied to the transducer 8b of the surface acoustic wave device 8. The stirring area is not limited to the area corresponding to the four positions of P2 to P5. Alternatively, if required, an area larger or smaller than the area corresponding to the four positions P2 to P5 can be set as the stirring area.

As shown in FIG. 3, the signal generator 22 is connected between the contact electrodes 21a and 21b with a wiring 22a. The signal generator 22 outputs a high-frequency signal of some tens MHz to some hundreds MHz to the surface acoustic wave device 8 based on a control signal from the drive control circuit 23, so that the transducer 8b generates acoustic waves (bulk wave $W_b$).

The drive control circuit 23 controls signals for driving the surface acoustic wave device 8. For example, an electronic control unit (ECU) in which a memory and a timer are installed is used as the drive control circuit 23. As shown in FIG. 3, the drive control circuit 23 is connected to the specimen dispensing mechanism 5 via the control unit 16. The drive control circuit 23 controls the signal generator 22, and outputs a control signal for controlling the signal generator 22 to the control unit 16, which ensures timing at which the control unit 16 controls the specimen dispensing mechanism 5. Similarly, the drive control circuit 23 ensures control timing at which the control unit 16 controls the reagent dispensing mechanism 12. The drive control circuit 23 controls, for example, characteristics (frequency, intensity, phase, wave characteristics), wave form (for example, sine wave, triangle wave, square wave, or burst wave), or modulation (amplitude modulation, or frequency modulation) of acoustic waves generated by the surface acoustic wave device 8. The drive control circuit 23 can change the frequency of an oscillation signal generated by the signal generator 22 according to the timer installed in the drive control circuit 23.

In the automatic analyzer 1 having the above configuration, the reagent dispensing mechanism 12 sequentially dispenses the reagent from the predetermined reagent vessel 14 to the reaction vessels 7 that are conveyed in the circumferential direction of the reaction wheel 6 with the rotation of the reaction wheel 6. After the reagent is dispensed to the reaction vessels 7, the reaction vessels 7 are conveyed to a position near the specimen dispensing mechanism 5 along with the rotation of the specimen table 3 and the specimen dispensing mechanism 5 sequentially dispenses the specimen from the specimen vessels 4 of the specimen table 3 to the reaction vessels 7.

Thereafter, while the reaction vessel 7 is conveyed in the circumferential direction of the reaction wheel 6 along with the rotation of the reaction wheel 6, the reagent and the specimen are stirred in the reaction vessels 7 by the stirring unit 20 and react, which results in a reaction solution. While the reaction vessel 7 is conveyed between the light source and the light receiving device, the light receiving device measures the light having penetrated through the reaction solution and the analyzing unit 16a analyzes the reaction solution and obtains, for example, the component density. Thereafter, the suction nozzle sucks and removes the reaction solution from the reaction vessel 7 and the reaction vessel 7 is cleaned by the detergent and washing water discharged by the discharge nozzle 10b. After being cleaned, the reaction vessels 7 are used again for analyzing a specimen.

Figure 9:
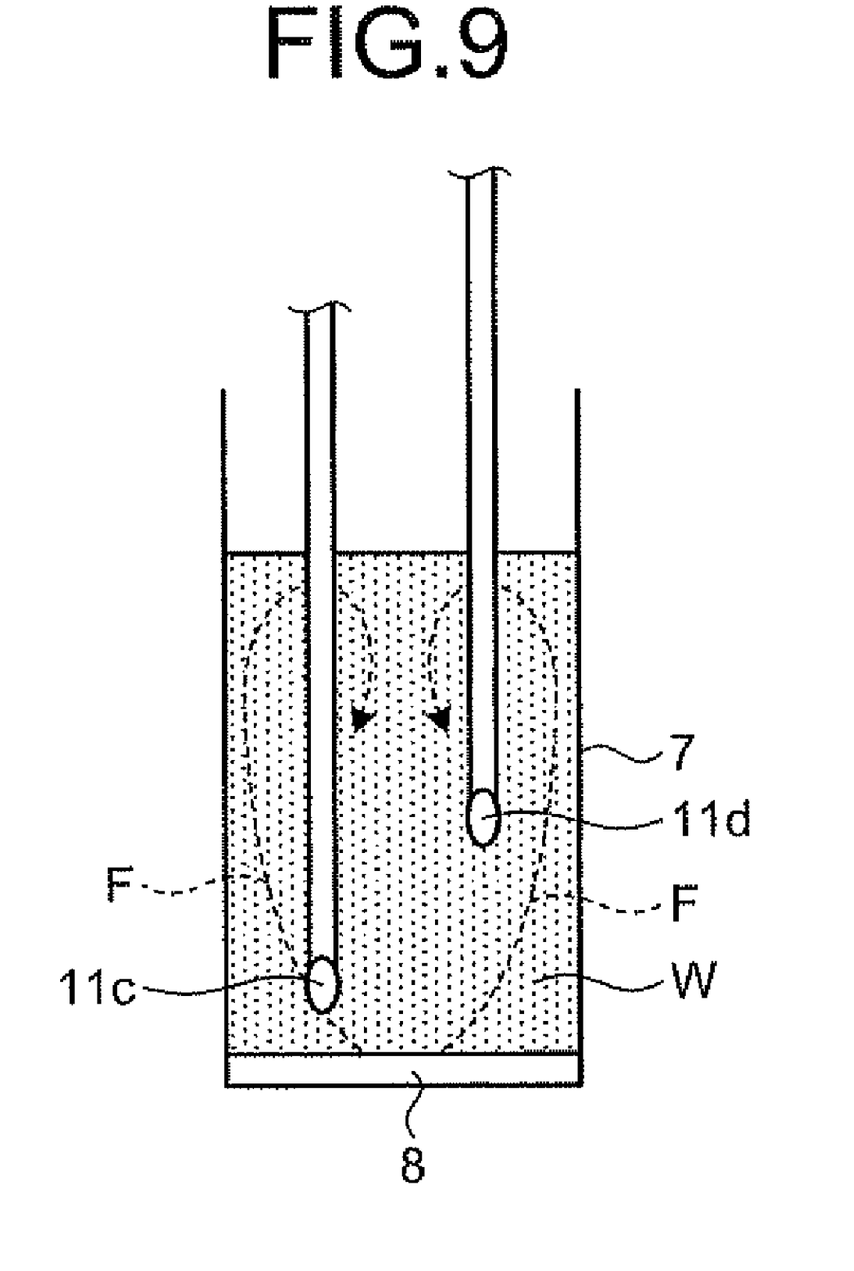
FIG. 9 is a schematic cross sectional view for illustrating stirred flows caused in the reaction vessel in which the temperature sensor is inserted.

The temperature sensors 11c and 11d are provided to the cleaning unit 10 to which the stirring unit 20 is provided. By driving the stirring unit 20 when the cleaning unit 10 cleans the reaction vessel 7, the surface acoustic wave device 8 is caused to generate the acoustic waves. The acoustic waves cause stirred flows denoted by F shown in FIG. 9 in the washing water contained in the reaction vessel 7 as shown in FIG. 9, which increases the temperature of the cleaning water. The temperature increasing rate varies in different positions in the vertical direction depending on whether the washing water is properly stirred. For this reason, whether the washing water is properly stirred can be determined based on the temperature increasing rate in different positions in the vertical direction in the reaction vessel 7.

Figure 10:
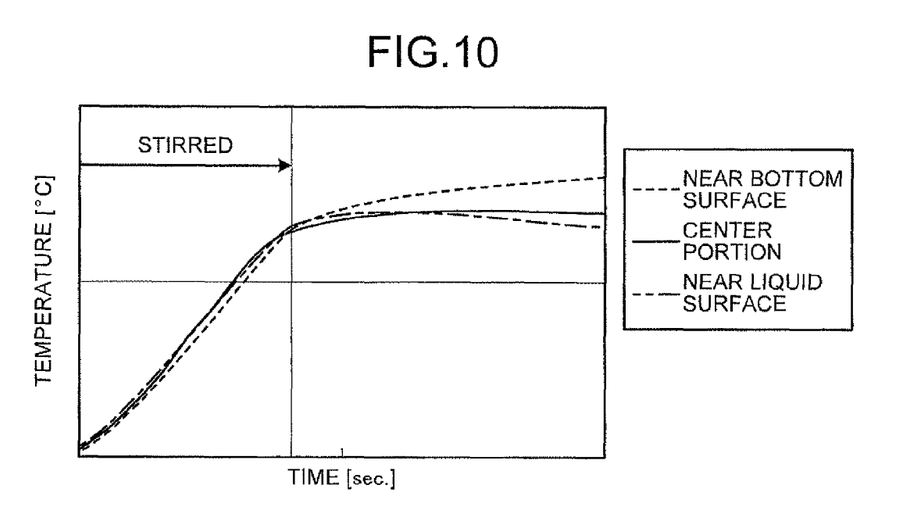
FIG. 10 shows variations in the temperature of washing water contained in the reaction vessel when the washing water is properly stirred.

Specifically, when the stirring unit 20 properly stirs the washing water in the reaction vessel 7, the temperature of the washing water linearly increases as shown in FIG. 10 while the washing water is stirred excluding the short period (about 100 milliseconds after the stirring is started) necessary for stabilizing the stirred flows. As a result, the temperature increasing rate is same in a position near the bottom surface of the reaction vessel 7, in a center position in the reaction vessel 7, and in a position near the liquid surface. The washing water is properly stirred when the relationship between the amount, specific gravity, and viscosity of the washing water and conditions on, for example, power and frequency for driving the surface acoustic wave device 8 is appropriate. The relationship varies depending on a liquid to be stirred.

Figure 11:
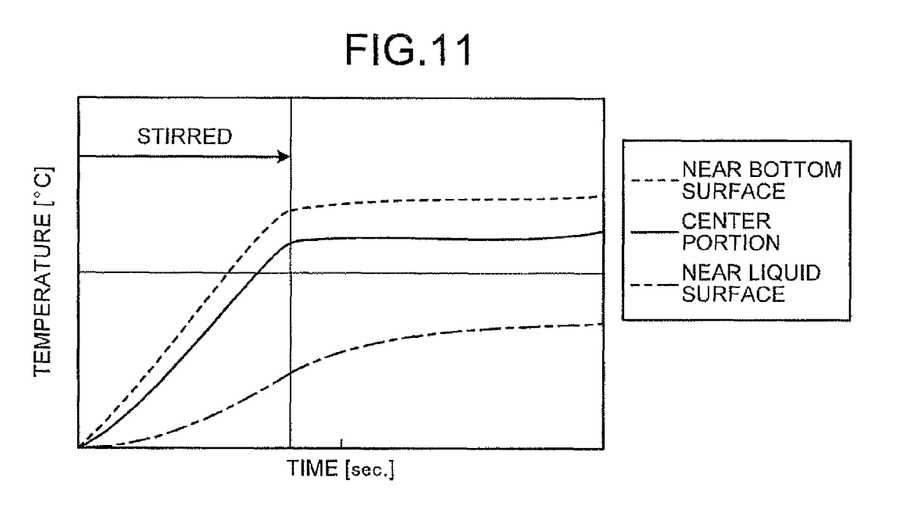
FIG. 11 shows variations in the temperature of washing water contained in the reaction vessel when the washing water is not properly stirred.

On the other hand, when the washing water is not properly stirred, the temperature of the washing water varies depending on the stirred flows and the distance from the position where heat is generated due to attenuation of the acoustic waves generated by the surface acoustic wave device 8. Specifically, the temperature of the washing water is different in the position near the bottom surface of the reaction vessel 7, in the center position in the reaction vessel 7, and the liquid surface, and furthermore, the temperature increasing rate is different in different positions in the vertical direction in the reaction vessel 7.

When the temperature of a liquid contained in the reaction vessel 7 is measured in at least two different positions in the vertical direction while the liquid is stirred, and if the liquid is properly stirred, the temperature increasing rate is same in the different positions. On the other hand, if the liquid is not properly stirred, the temperature increasing rate is different between the different positions. For this reason, in the automatic analyzer 1, the temperature of the fluid in the reaction vessel 7 is measured in at least two different positions in the vertical direction while the liquid is stirred. When the liquid is properly stirred, the temperature increasing rate is stable while the liquid is stirred not depending on the passage of time as shown in FIG. 10. For this reason, the temperature of the liquid can be measured in different positions in the vertical direction simultaneously or at different timing.

Figure 12:
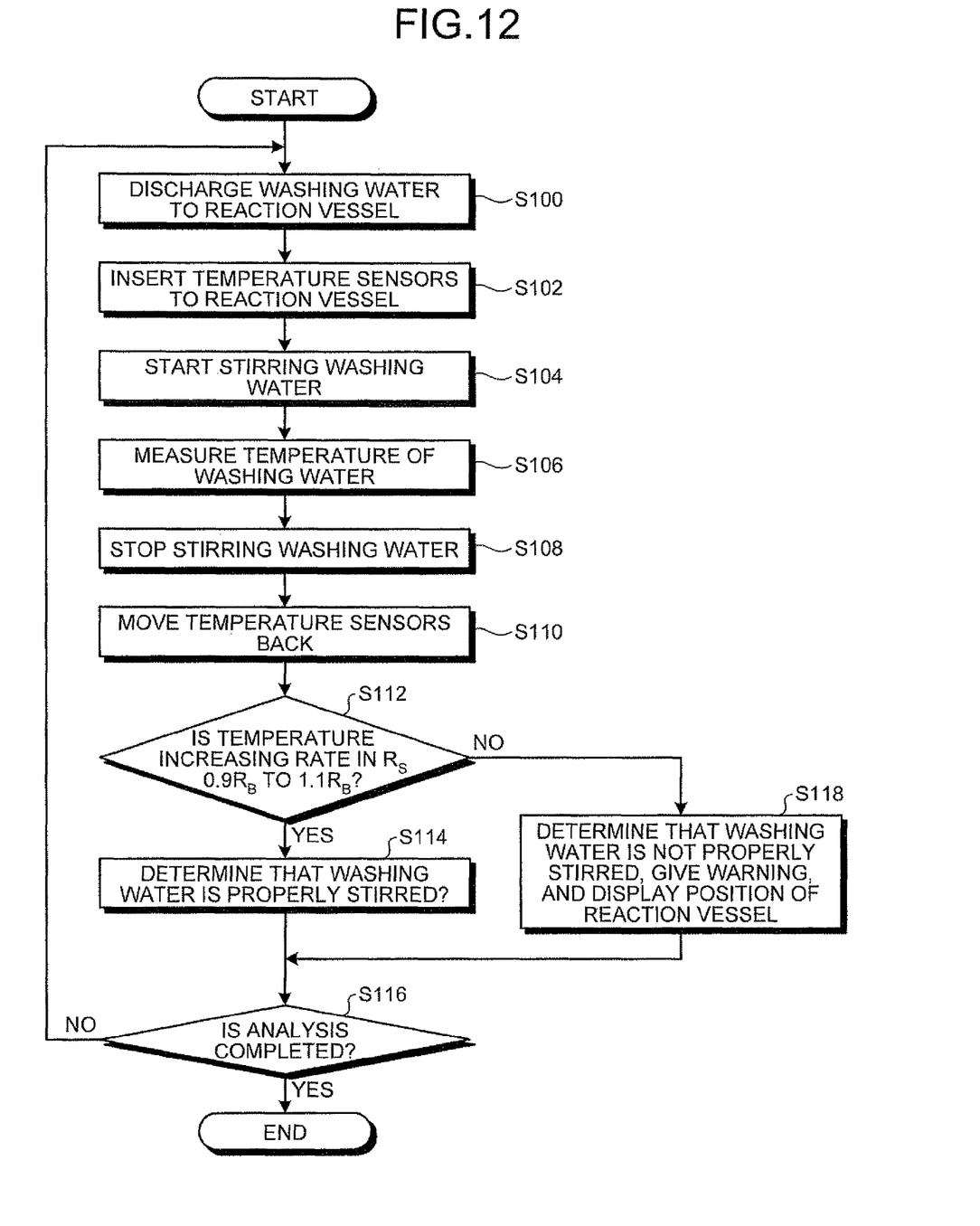
FIG. 12 is a flowchart of a stirring determination method according to the first embodiment.
Figure 13:
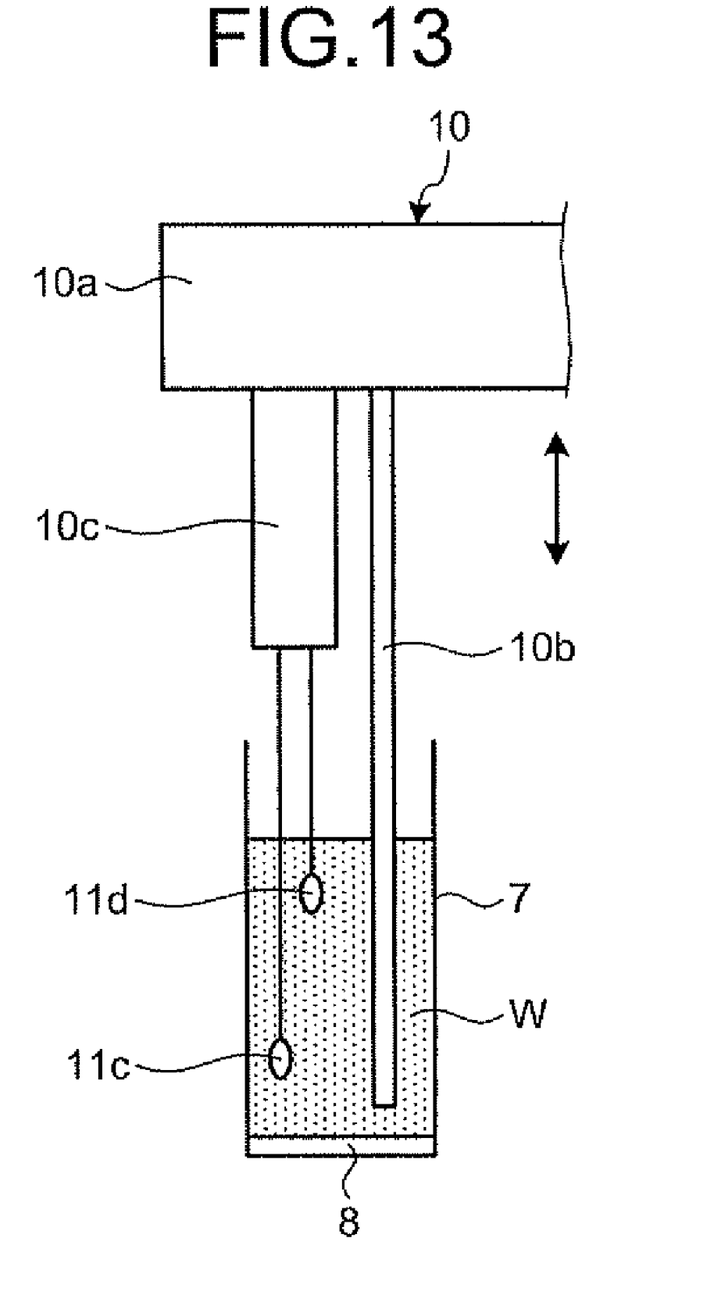
FIG. 13 is a schematic cross sectional view of a reaction vessel into which a discharge nozzle of a cleaning unit and a temperature sensor of a temperature measuring unit are inserted, for illustrating Modified example 1 of the automatic analyzer according to the first embodiment.

In response to an instruction for performing the stirring determination (i.e., for determining whether the liquid is properly stirred) received from the input unit 17 during the analysis operation, the stirring determination is performed according to the flowchart shown in FIG. 12 under the control of the control unit 16 in parallel with the analysis operation.

The control unit 16 causes the cleaning unit 10 to discharge the washing water to the reaction vessel 7 when the reaction wheel 6 is stopped (step S100). The control unit 16 causes the temperature measuring unit 11 to insert the temperature sensors 11c and 11d into the reaction vessel 7 (step S102).

The control unit 16 causes the stirring unit 20 provided to the cleaning unit 10 to start stirring the washing water in the reaction vessel 7 (step S104). While the washing water is stirred, the control unit 16 measures the temperatures of the washing water (step S106). At step S106, whether the washing water is properly stirred is determined based on the temperature increasing rate obtained from the temperature measured by the temperature sensor 11c at predetermined intervals and on the temperature increasing rate obtained from the temperature measured by the temperature sensor 11d at predetermined intervals.

Thereafter, the control unit 16 causes the stirring unit 20 to stop stirring the washing water (step S108). The control unit 16 causes the temperature measuring unit 11 to extract the temperature sensors 11c and lid from the reaction vessel 7 and move the original positions back (step S110).

The control unit 16 determines whether a temperature increasing rate $R_S$ at the position near the liquid surface of the washing water with respect to a temperature increasing rate $R_B$ at the position near the bottom of the reaction vessel 7 is $0.9R_B$ to $1.1R_B$ (step S112). Specifically, the above determination is made by the determining unit 16b. The temperature increasing rates $R_S$ and $R_B$ are obtained by the control unit 16 based on the temperature of the washing water measured by the temperature sensors 11c and 11d in the different positions in the vertical direction at predetermined intervals.

When the temperature increasing rate $R_S$ is $0.9R_B$ to $1.1R_B$ (YES at step S112), the control unit 16 determines that the washing water is properly stirred (step S114). Thereafter, the control unit 16 determines whether analysis on all specimens is completed (step S116). When analysis on all specimen is completed (YES at step S116), the control unit 16 completes the stirring determination. On the other hand, when the determination on all specimens is not completed (NO at step S116), the control unit 16 goes back to step S100.

At step S112, when the temperature increasing rate $R_S$ is not $0.9R_B$ to $1.1R_B$ (NO at step S112, the control unit 16 determines that the washing water is not properly stirred and attaches a warning to the result of analyzing the specimen using the reaction vessel 7 and causes the display unit 18 to display the position of the reaction vessel (step S118). When the temperature increasing rate $R_S$ is not $0.9R_B$ to $1.1R_B$, $0.9R_B > R_S$ is satisfied. $R_S > 1.1R_B$ is not satisfied because the surface acoustic wave device 8 is attached to the bottom wall of the reaction vessel 7. After step S118, the control unit 16 goes to step S16 and completes the stirring determination. When it is determined twice, on the same reaction vessel, that the washing water is not properly stirred, the control unit 16 prohibits using the reaction vessel 7 for analyzing a specimen.

As explained above, with respect to the stirring determination method and the automatic analyzer 1, the temperature of the washing water is measured in at least two different position in the vertical direction while the washing water is stirred, and whether the washing water is properly stirred is determined based on the temperature increasing rate obtained from the measured temperature of the washing water. This makes it easier to assuredly determine whether the washing water is properly stirred.

Modified Example 1

Figure 14:
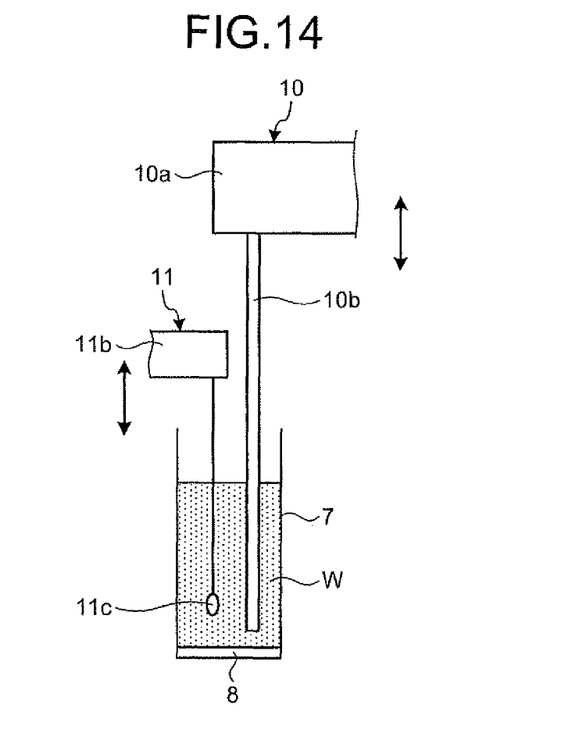
FIG. 14 is a schematic cross sectional view of a reaction vessel into which a discharge nozzle of a cleaning unit and a temperature sensor of a temperature measuring unit are inserted, for illustrating Modified Example 2 of the automatic analyzer according to the first embodiment.

The temperature sensors 11c and 11d can hang from a supporting member 10c provided to the elevating member 10a and configured to move integrally with the cleaning unit 10 as shown in FIG. 14. In this configuration, the structure of the temperature measuring unit can be compact compared with the case where the temperature measuring unit 11 is independently provided.

Modified Example 2

Alternatively, the temperature measuring unit 11 can be configured as shown in FIG. 14. In this configuration, only the temperature sensor 11c is provided to the holding arm 11b. By causing the holding arm 11b move down while the stirring unit 20 stirs the washing water, the temperature of the washing water in two different positions in the vertical direction can be measured. In this configuration, the structure of the temperature measuring unit 11 can be more compact.

Figure 15:
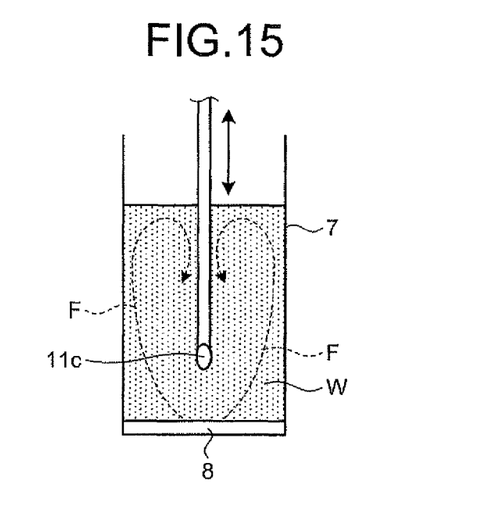
FIG. 15 is a schematic cross sectional view for illustrating stirred flows caused in the reaction vessel shown in FIG. 14 in which the temperature sensor is inserted.

In this configuration, when the stirring unit 20 drives the surface acoustic wave device 8, the stirred flows, which is denoted by F shown in FIG. 15, is caused in the washing water discharged to the reaction vessel 7, which is denoted by W shown in FIG. 15, and the stirred flows increase the temperature of the washing water. Therefore, for example, after the temperature measuring unit 11 measures the temperature of the washing water for 1 second at the position 1 millimeters above the bottom surface of the reaction vessel 7, the holding arm 11b is moved up and the temperature measuring unit 11 measures the temperatures of the washing water for 1 second in the position 3 millimeters above the bottom surface of the reaction vessel 7. The temperature increasing rate is obtained based on the measured temperature of the washing water, and whether the washing water is properly stirred is determined.

Modified Example 3

Figure 16:
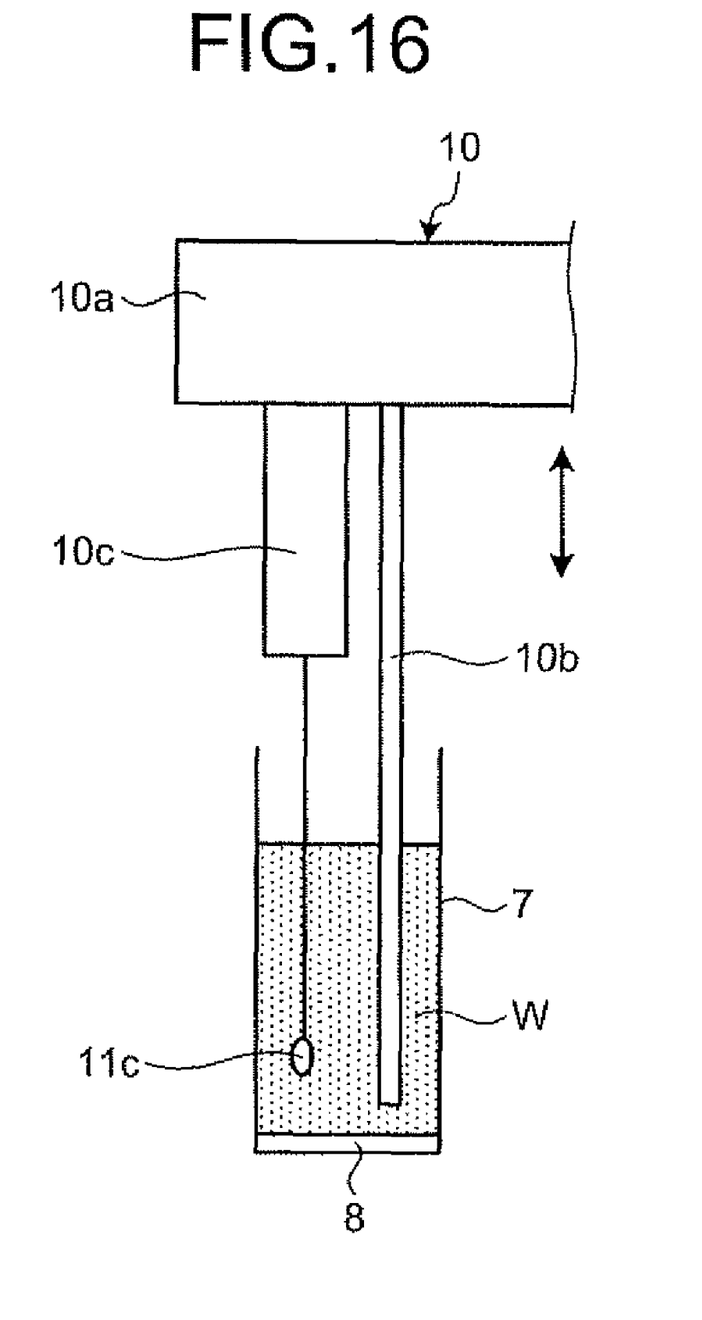
FIG. 16 is a schematic cross sectional view of a reaction vessel into which a discharge nozzle of a cleaning unit and a temperature sensor of a temperature measuring unit are inserted, for illustrating Modified Example 3 of the automatic analyzer according to the first embodiment.

Alternatively, the temperature sensor 11c can hang from the supporting member 10c provided to the elevating member 10a as shown in FIG. 16 and can be configured to move integrally with the cleaning unit 10. In this configuration, the structure of the temperature measuring unit 11 can be more compact compared with the case where the temperature measuring unit 11 is independently provided.

Figure 17:
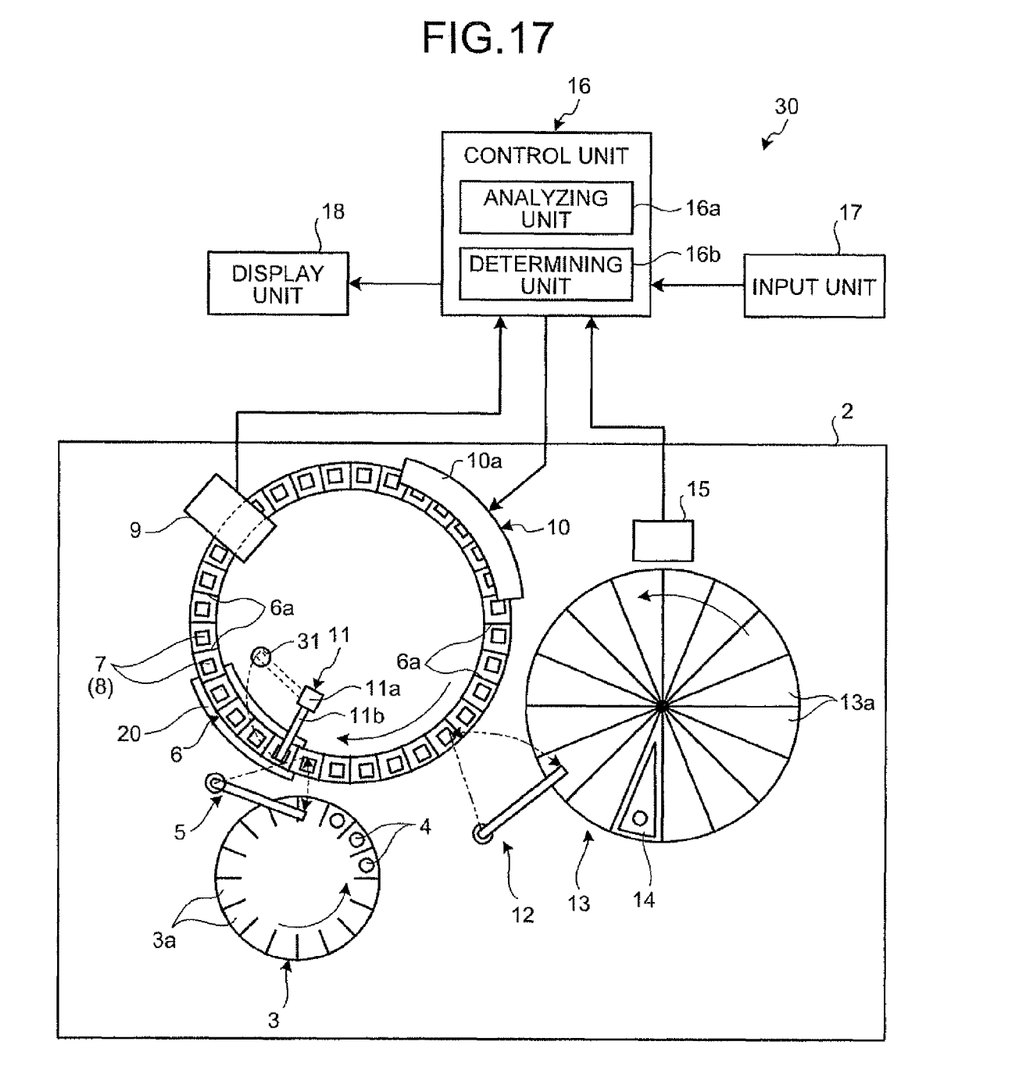
FIG. 17 is a schematic diagram of an automatic analyzer according to a second embodiment of the present invention.

An automatic analyzer 30 according to a second embodiment of the present invention is explained in detail below with reference to the drawings. In the automatic analyzer 1 according to the first embodiment, the temperature measuring unit and the stirring unit are provided to the cleaning unit, and the stirring unit is additionally provided. On the other hand, in the automatic analyzer 30 according to the second embodiment, the temperature measuring unit is provided to the stirring unit 20. FIG. 17 is a schematic diagram of the automatic analyzer 30. The reference numerals for the automatic analyzer 30 shown in FIG. 17 that are the same as those for the automatic analyzer 1 shown in FIG. 1 denote respectively the same constituents as those of the automatic analyzer 1.

As shown in FIG. 17, in the automatic analyzer 30, the stirring unit 20 and the temperature measuring unit 11 are arranged near the specimen dispensing mechanism 5. The temperature measuring unit 11 includes a cleaning tank 31 for cleaning the temperature sensors 11c and 11d on the orbit on which the holding arm 11b rotates on the support column 11a. Washing water is discharged to the cleaning tank 31, and the temperature sensors 11c and 11d having been inserted into the reaction vessel 7 containing a liquid sample of a reagent and a specimen, which is denoted by Ls shown in FIG. 16, is cleaned in the cleaning tank 31 with the washing water.

Figure 18:
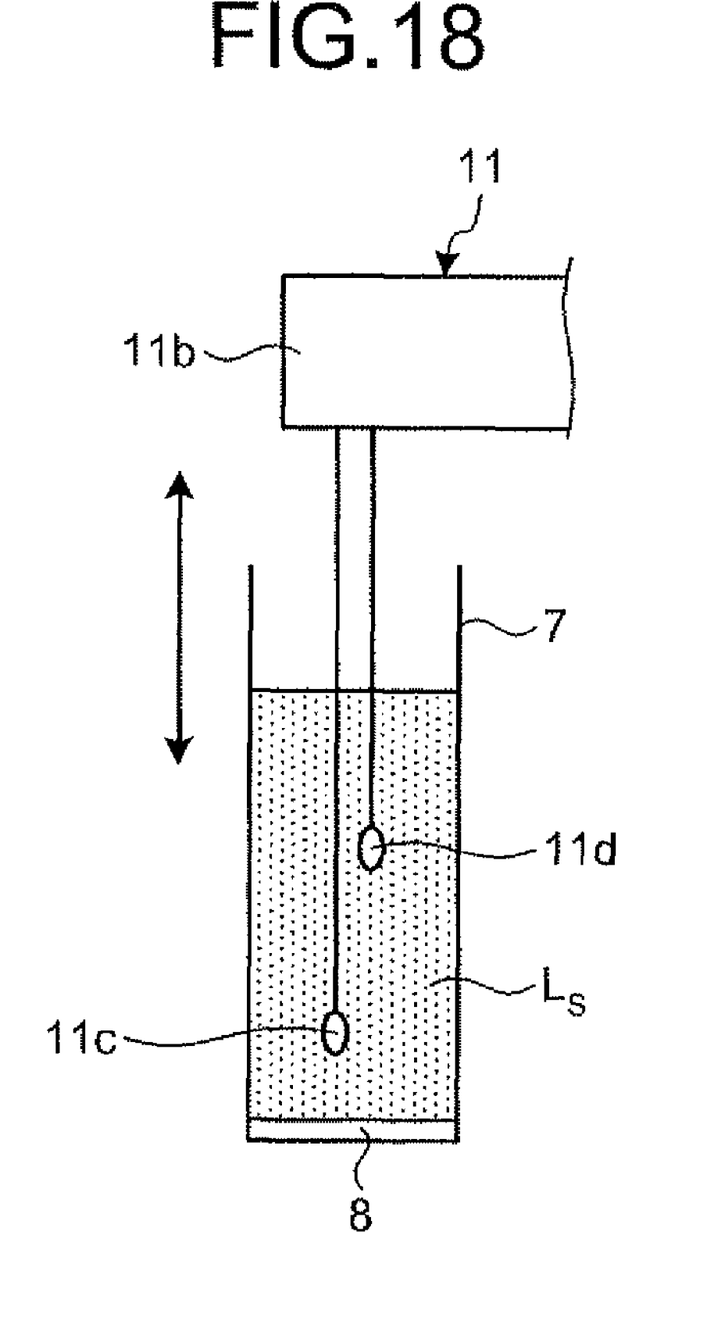
FIG. 18 is a schematic diagram of a reaction vessel shown in FIG. 17 into which a temperature sensor is inserted.

In the automatic analyzer 30, in response to an instruction for performing stirring determination received from the input unit 17 during an analysis operation, the temperature sensors 11c and 11d measure the temperature of the liquid sample of the reagent and the specimen as shown in FIG. 18 while the stirring unit 20 stirs the liquid sample in parallel with the operation for analyzing the specimen. Based on the measured temperature, the control unit 16 (determining unit 16b) determines whether the liquid sample is properly stirred by the stirring determination method explained above.

The temperature measuring unit 11 can include only the temperature sensor 11c as shown in FIGS. 14 to 16. In this case, by moving down the temperature sensor 11c while the stirring unit 20 stirs the liquid sample, the temperature of the liquid sample is measured at different timing in at least two different positions in the vertical direction, and whether the liquid sample is properly stirred is determined based on the measured temperature.

The automatic analyzer 30 has, in addition to a normal analysis mode, a special mode such as a maintenance mode for maintenance inspection or a diagnostic mode (DIAG mode) in which the automatic analyzer 30 operates in a different manner from that of the analysis operation. When the operation mode of the automatic analyzer 30 is switched to the special mode, after a reagent, a specimen, washing water, or a liquid to which stirring is evaluated is dispensed into the reaction vessel 7 and while the stirring unit 20 stirs the liquid, the temperature of the liquid is measured in two different positions in the vertical directions and whether the liquid is properly is stirred is determined based on the measured temperature.

In the first and second embodiments, whether the liquid is properly stirred is determined based on the temperature increasing rates obtained from the temperature of the liquid measured at different two positions, i.e., the position near the bottom surface and the position near the liquid surface. However, it suffices that whether liquid is properly stirred be determined based on the temperature increasing rate obtained from the temperature of the liquid in the position where the temperature is different before and after the liquid is stirred. For example, as explained with reference to FIGS. 10 and 11, the temperature of the liquid is measured in the position near the liquid surface and whether the liquid is properly stirred can be determined based on the temperature increasing rate obtained from the measured temperature of the liquid.

For simple explanation on the automatic analyzers 1 and 30, the stirring unit arranged in one position is explained. However, a plurality of stirring units can be arranged in a plurality of positions. Furthermore, as the reagent table 13, a plurality of regent tables such as a first reagent table and a second reagent table can be used.

The surface acoustic wave device 8 can be attached to a side surface of the reaction vessel 7 instead of the bottom surface of the reaction vessel 7.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A stirring determination method using an analyzer in which washing water contained in a vessel is stirred by an acoustic wave generated by an acoustic wave generating unit attached to the vessel, the stirring determination method comprising:
    measuring a rate of increase of temperature of the washing water in at least two different spatial positions where temperature of the washing water is different before and after the washing water is stirred; and
    determining whether the washing water is properly stirred by comparing the measured rates of increase of the temperature of the washing water in the at least two different spatial positions, wherein the determining is used to indicate whether a result of analyzing a liquid in the vessel is suspect.

2. The stirring determination method according to claim 1, wherein
    the acoustic wave generating unit is attached to a bottom surface of the vessel, and
    the at least two different spatial positions are at least two different spatial positions in a vertical direction while the washing water is stirred.

3. The stirring determination method according to claim 2, wherein
    the determining includes determining that the washing water is properly stirred when $0.9R_B \leq R_S \leq 1.1R_B$ and determining that the washing water is not properly stirred when $0.9R_B > R_S$, where $R_S$ is a rate of increase in the temperature of the washing water in a position near a surface of the washing water, and $R_B$ is a rate of increase in the temperature of the washing water in a position near the bottom surface of the vessel.

4. The stirring determination method according to claim 1, further comprising adding a warning to a result of analyzing a liquid in the vessel and displaying a position of the vessel when the determining includes determining that the washing water is not properly stirred.

5. The stirring determination method according to claim 1, further comprising prohibiting using the vessel when the determining includes determining twice that the washing water is not properly stirred.

6. The stirring determination method according to claim 1, wherein the rate of increase of temperature of the washing water in the at least two different spatial positions is measured by at least one sensor located in the washing water.

* * * * *